US00PP07872P

United States Patent [19]

Belgiorno

[11] Patent Number: Plant 7,872

[45] Date of Patent: May 26, 1992

[54] *PIERIS JAPONICA* NAMED SWEETWATER

[76] Inventor: Carlo Belgiorno, 1165 Connetiquot Ave., Central Islip, N.Y. 11722

[21] Appl. No.: 572,766

[22] Filed: Aug. 27, 1990

[51] Int. Cl.[5] ..... A01H 5/00
[52] U.S. Cl. ..... Plt./54
[58] Field of Search ..... Plt. 54

[56] References Cited

U.S. PATENT DOCUMENTS

P.P. 3,339 5/1973 Bosley ..... Plt. 54
P.P. 4,794 11/1981 Verkade ..... Plt. 54

*Primary Examiner*—James R. Feyrer
*Attorney, Agent, or Firm*—Edward H. Loveman

[57] ABSTRACT

A new and distinct *Pieris japonica* was discovered which has sterile blooms and a sweet fragrance and has longer than average blooming time and has been asexually reproduced.

2 Drawing Sheets

BACKGROUND OF THE INVENTION

This invention relates to a new and distinct variety of *Pieris japonica,* commonly known as Andromeda, and more particularly concerns a *Pieris japonica* whose flower has a sweet fragrance.

SUMMARY OF THE INVENTION

The invention was discovered by me as a chance seedling at my nursery located at 1165 Connetiquot Avenue, Central Islip, N.Y. 11722.

As a 3 year old seedling it had grown larger than average size in a bed of many *Pieris japonica* seedlings, and it had exhibited a vigorous growing habit. This seedling first flowered between its 4th and 5th year. The flowers looked identical to other *Pieris japonica* flowers with the start of the bloom at the same time as that of other *Pieris japonica.* However, the flowers are perfect lasted longer, 5 to 6 weeks of blooms have been observed, and flowers also have a sweet fragrance.

The plant blooms in one heavy flush extending five to six weeks every year but is generically sterile and thus no seed pods are produced just a few undeveloped green pods that quickly fall off. The plant has never produced seeds so the flowers are sterile. The strong sweet fragrance of the flowers is much stronger than those of other *Pieris japonica's* and is similar to the smell of honeysuckle. The plant is much more vigorous with regard to other *Pieris japonica's* such as Forest Flare, Mountain Fire, or Crystal. The plant appears to have many more leaves than conventional *Pieris japonica's.* The energy of the plant goes into the vegetative growth of the plant which yields more leaves than other *Pieris japonica's* and a heavy flower set each year and perhaps more importantly substantially increases the plant's resistance to disease and insect problems.

BRIEF DESCRIPTION OF THE DRAWINGS

The first sheet of the accompanying illustration, in full color, shows a typical specimen of the entire plant as close to the natural colors as can be reproduced by this method.

The second sheet of the drawing is a close-up view of a single branch of 'Sweetwater' is depicted against a white background, showing leaves in greater detail and also depicts the character of the flower parts in a late summer, early fall growth stage.

The following is a detailed description of the plant and its flower:

THE PLANT

Type: Broad leaf evergreen, vigorous and full compact growth habit, which has sterile white flowers with a long blooming time and a sweet fragrance. The plant is more basically dominant having many more primary stems with more branches than other varieties of Andromeda's. The leaf dimensions are 5.8 cm × 1.6 cm with a leaf thickness varying from 0.35 mm–0.39 mm. The petiole is 7 mm long and the cuticle thickness ranges from 5.0–7.5 microns. The leaf margin is dominated by alternating minor teeth or dentations. Both the upper and lower surface of the leaves are covered with glandular hairs (62 microns long, unevenly scattered). The swelling at the tip of the hair (37.5 microns long) is dark red on the hairs on the leaf's underside, and more blackish on the hairs on the upper surface. Similar glandular hairs also occur regularly along the leaf edge, on the end of the dentations, but these hairs have longer stalks. There are stomata irregularly scattered across the leaf undersurface, generally ranging from 5–37 microns apart from one another. The guard cells form a nearly circular shape (30 microns × 27.5 microns). The upper leaf color is Green 138B; the lower leaf color is 143C; the leaf stem color is 142D. The leaves remain on the plant for three complete seasons before shedding. The flowers are perfect having stamens and a pistil. The pollen grains are 25 microns in diameter. The rosettes contain 8–12 leaves. The bark is striped with the old growth a dark brown color 199B and the new growth 199D. The flower color is 155B and the Raceme color is red 44C during winter and during spring when the flower blooms the Raceme Color is 154D. The flower count is the heaviest of any known *Pieris japonica's,* 10–15% larger than the conventional Andromeda's.

Parentage: *Pieris japonica.* The original plant is a selected seedling that was sown and grown at a nursery located at 1165 Connetiquot Avenue, Central Islip, N.Y.

Growth habit: Grows vigorous, full and compact with a glossy and wavy foliage. The growth is heavy with no shaping. Blooms are heavy each year with no seed production.

Size: The original plant is after 30 plus years, 6 foot wide and 6 foot high and is multi-stemed.

Spread of plant: In 6–8 years the plant will average a spread of 3 feet.

Height of plant: This plant will average 3 feet high in 6–8 years.

Hardiness: The original plant has been growing in a location where it can experience sunlight throughout the day. The temperature has ranged from a high of 102° F. to a low of 18° F. below zero. In particular, during December 1989 the plant was exposed to below freezing temperatures as low as 12° F. to 18° F. below zero for over 3½ weeks and nonetheless during the spring of 1990 the plant bloomed fully with no leaf burn.

Propagation: Cuttings taken in late fall and early winter, which are treated with #3 I.B.A. or Dip N' Grow of 1–8 or 1–9 ratio, root with no difficulty. The cuttings are placed in a peat moss perlite half and half mix, maintained at 70° F. Since the plant is a broad leaf evergreen it may also be propagated by tissue culture.

Insect and diease problems: The original plant was removed from the producing area 24 years ago and no sprays of any kind have have been applied to it during this period of time. It has grown well without the sprays, and is resistant to lace wing fly, a major insect pest for *Pieris japonica.*

Production methods: The plant fits in well to field growing and grows well in potting mixes for container growing and potted liner production. Since the plant is a broadleaf evergreen, it may be tissue cultured.

Pruning and trimming: Very little prunning is required except for a particular desired shape. There is a great deal of labor saved because the flowers are sterile and thus there are no seed pods for growers to remove each year in order to promote full plant growth as is normally the case on regular *Pieris japonica.*

Descendants: The plant is a selected seedling and all rooted cuttings have all of its characteristics.

Blooms: The flower color is white and the flowers are sterile and have a longer than average blooming time i.e. 5–6 weeks. They also have a sweet fragrance. The stalk supporting the cluster of buds is a light red color which adds interest and beauty to the plant in the fall and winter season and at blooming time.

Genus: *Pieris japonica.*

Genus of parent: *Pieris japonica,* source of seed was from open pollination.

I claim:

1. A new and distinct *Pieris japonica* substantially as herein shown and described characterized particularly by the unique combination and distinctive characteristics of dense vigorous growth, with heavy blooms every year, and sterile flowers having a sweet fragrance which bloom for longer periods than other *Pieris japonica.*

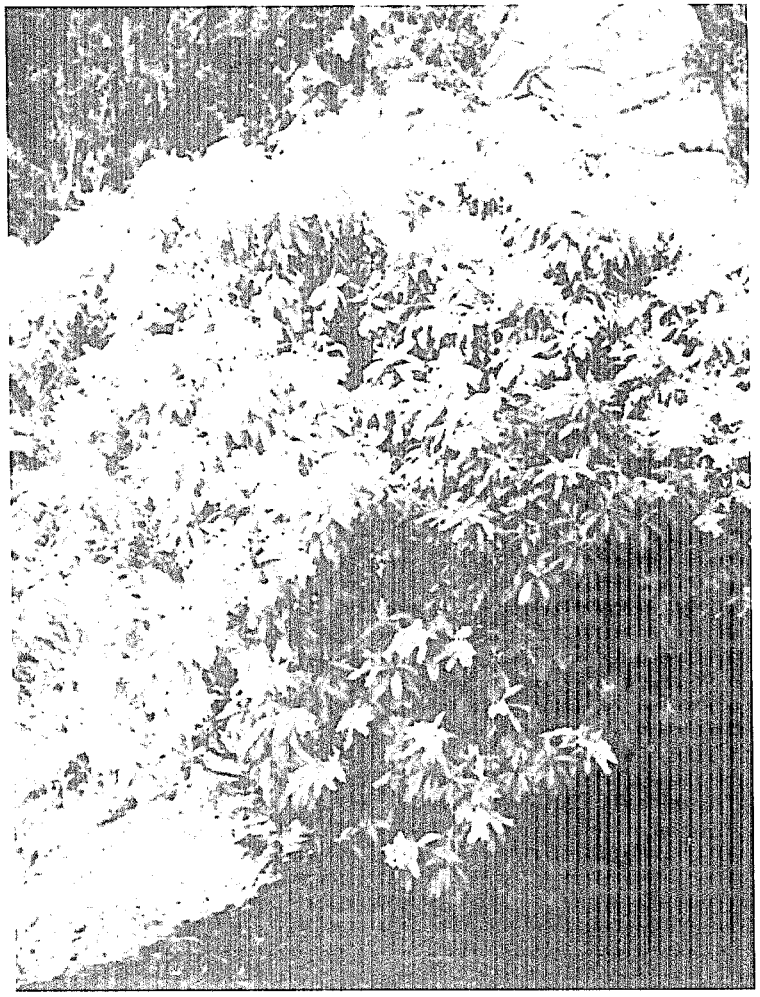

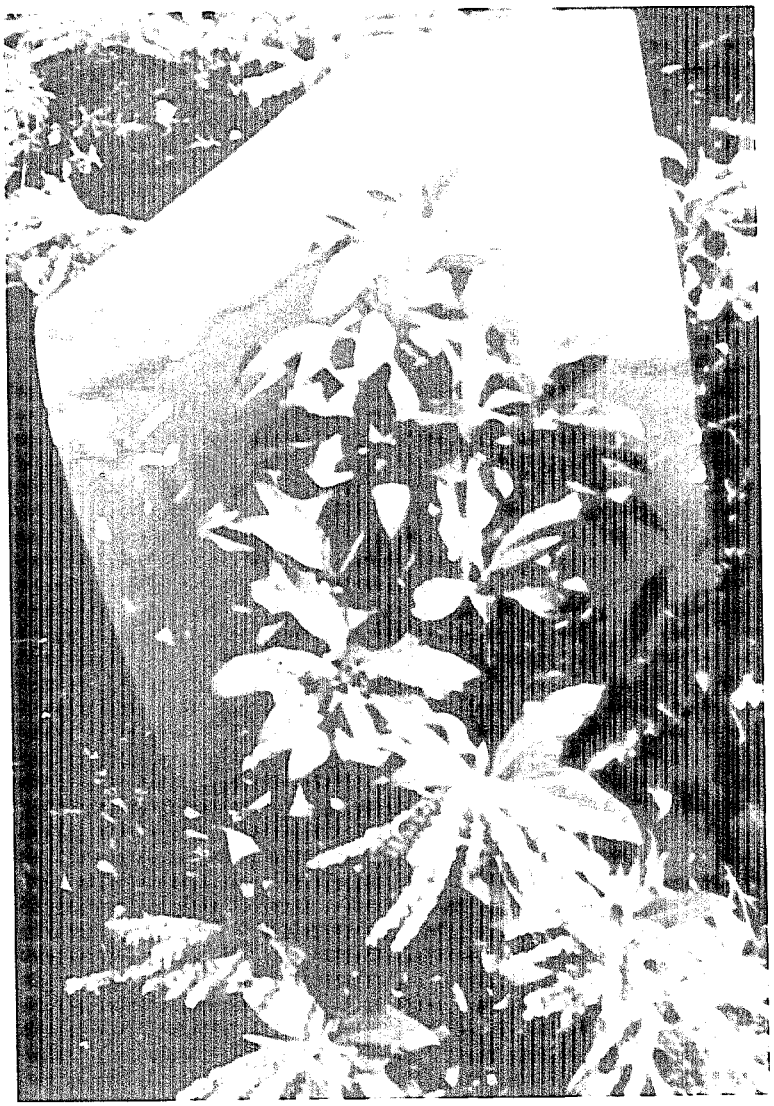

* * * * *